US009277995B2

(12) United States Patent
Celermajer et al.

(10) Patent No.: US 9,277,995 B2
(45) Date of Patent: Mar. 8, 2016

(54) DEVICES AND METHODS FOR REDUCING VENOUS PRESSURE (75) Inventors: David Celermajer, Vaucluse (AU); Michael W. Sutherland, Pelham, NH (US); Edward McNamara, Chelmsford, MA (US)

(73) Assignee: Corvia Medical, Inc., Tewksbury, MA (US)

( * ) Notice: Subject to any disclaimer, the term of this patent is extended or adjusted under 35 U.S.C. 154(b) by 0 days.

(21) Appl. No.: 13/016,290

(22) Filed: Jan. 28, 2011

(65) Prior Publication Data

US 2011/0190874 A1    Aug. 4, 2011

Related U.S. Application Data (60) Provisional application No. 61/299,656, filed on Jan. 29, 2010.

(51) Int. Cl.
*A61F 2/24* (2006.01)

(52) U.S. Cl.
CPC .............. *A61F 2/2475* (2013.01); *A61F 2/2418* (2013.01); *A61F 2/2412* (2013.01); *A61F 2210/0014* (2013.01); *A61F 2220/0008* (2013.01); *A61F 2220/0016* (2013.01); *A61F 2220/0075* (2013.01); *A61F 2250/0029* (2013.01); *A61F 2250/0036* (2013.01)

(58) Field of Classification Search
CPC .................................................... A61F 2/2412
USPC ................. 623/1.24, 1.26, 2.1–2.19
See application file for complete search history.

(56) References Cited

U.S. PATENT DOCUMENTS

| 3,874,388 A | 4/1975 | King et al. |
| 4,018,228 A | 4/1977 | Goosen |
| 4,373,216 A | 2/1983 | Klawitter |
| 4,491,986 A * | 1/1985 | Gabbay ........................ 623/2.18 |

(Continued)

FOREIGN PATENT DOCUMENTS

| AU | 2007317191 A1 | 5/2008 |
| CN | 1218379 A | 6/1999 |

(Continued)

OTHER PUBLICATIONS

International Search Report, PCT/AU/01704, Mailed Jan. 16, 2008, 4 pages.

(Continued)

*Primary Examiner* — Yashita Sharma
*Assistant Examiner* — Rebecca Preston
(74) *Attorney, Agent, or Firm* — Shay Glenn LLP (57) ABSTRACT

Devices and method are disclosed for reducing pressure in a patient's vena cava and in the right atrium of a patient's heart. A valve is implanted in the inferior vena cava (IFC) between the patient's renal veins and hepatic veins. When pressure in a patient's IFC reaches high levels, i.e., the pressure differential across the valve reaches high levels, the valve automatically closes or begins to close. The closing is caused by the pressure of the patient's blood moving one or more flaps in the valve to a closed or near-closed position. This prevents excessive pressure in the upper or superior vena cava and the right atrium of the patient's heart. The device also includes a pressure relief feature that opens and allows retrograde flow of blood if the pressure differential exceeds a yet higher pressure.

11 Claims, 5 Drawing Sheets

(56) References Cited

U.S. PATENT DOCUMENTS

| | | |
|---|---|---|
| 4,705,507 A | 11/1987 | Boyles |
| 5,108,420 A | 4/1992 | Marks |
| 5,171,233 A | 12/1992 | Amplatz et al. |
| 5,284,488 A | 2/1994 | Sideris |
| 5,332,402 A | 7/1994 | Teitelbaum |
| 5,334,217 A | 8/1994 | Das |
| 5,413,599 A | 5/1995 | Imachi et al. |
| 5,429,144 A | 7/1995 | Wilk |
| 5,433,727 A | 7/1995 | Sideris |
| 5,464,449 A | 11/1995 | Ryan et al. |
| 5,478,353 A | 12/1995 | Yoon |
| 5,556,386 A | 9/1996 | Todd |
| 5,578,045 A | 11/1996 | Das |
| 5,693,090 A | 12/1997 | Unsworth et al. |
| 5,702,412 A | 12/1997 | Popov et al. |
| 5,725,552 A | 3/1998 | Kotula et al. |
| 5,824,071 A | 10/1998 | Nelson et al. |
| 5,846,261 A | 12/1998 | Kotula et al. |
| 5,876,436 A | 3/1999 | Vanney et al. |
| 5,893,369 A | 4/1999 | Lemole |
| 5,944,738 A | 8/1999 | Amplatz et al. |
| 5,964,754 A | 10/1999 | Osypka |
| 6,050,936 A | 4/2000 | Schweich, Jr. et al. |
| 6,059,827 A | 5/2000 | Fenton |
| 6,068,635 A | 5/2000 | Gianotti |
| 6,077,281 A | 6/2000 | Das |
| 6,120,534 A | 9/2000 | Ruiz |
| 6,123,715 A | 9/2000 | Amplatz |
| 6,152,937 A | 11/2000 | Peterson et al. |
| 6,156,055 A | 12/2000 | Ravenscroft |
| 6,168,622 B1 | 1/2001 | Mazzocchi |
| 6,190,353 B1 | 2/2001 | Makower et al. |
| 6,193,734 B1 | 2/2001 | Bolduc et al. |
| 6,210,338 B1 | 4/2001 | Afremov et al. |
| 6,241,678 B1 | 6/2001 | Afremov et al. |
| 6,258,119 B1 | 7/2001 | Hussein et al. |
| 6,286,512 B1 | 9/2001 | Loeb et al. |
| 6,334,864 B1 | 1/2002 | Amplatz et al. |
| 6,350,277 B1 | 2/2002 | Kocur |
| 6,355,052 B1 | 3/2002 | Neuss et al. |
| 6,355,056 B1 | 3/2002 | Pinheiro |
| 6,357,735 B2 | 3/2002 | Haverinen |
| 6,383,195 B1 | 5/2002 | Richard |
| 6,395,017 B1 | 5/2002 | Dwyer et al. |
| 6,402,777 B1 | 6/2002 | Globerman et al. |
| 6,409,716 B1 | 6/2002 | Sahatjian et al. |
| 6,440,152 B1 | 8/2002 | Gainor et al. |
| 6,454,795 B1 | 9/2002 | Chuter |
| 6,458,153 B1 * | 10/2002 | Bailey et al. ............... 623/1.24 |
| 6,468,301 B1 | 10/2002 | Amplatz et al. |
| 6,468,303 B1 | 10/2002 | Amplatz et al. |
| 6,527,746 B1 | 3/2003 | Oslund et al. |
| 6,572,652 B2 | 6/2003 | Shaknovich |
| 6,579,311 B1 | 6/2003 | Makower |
| 6,599,308 B2 | 7/2003 | Amplatz |
| 6,626,936 B2 | 9/2003 | Stinson |
| 6,638,257 B2 | 10/2003 | Amplatz |
| 6,641,610 B2 | 11/2003 | Wolf et al. |
| 6,645,143 B2 | 11/2003 | VanTassel et al. |
| 6,666,885 B2 | 12/2003 | Moe |
| 6,712,836 B1 | 3/2004 | Berg et al. |
| 6,719,768 B1 | 4/2004 | Cole et al. |
| 6,837,901 B2 | 1/2005 | Rabkin et al. |
| 6,866,679 B2 | 3/2005 | Kusleika |
| 6,911,037 B2 | 6/2005 | Gainor et al. |
| 6,913,614 B2 | 7/2005 | Marino et al. |
| 6,932,837 B2 | 8/2005 | Amplatz et al. |
| 6,936,058 B2 | 8/2005 | Forde et al. |
| 6,979,343 B2 | 12/2005 | Russo et al. |
| 7,001,409 B2 | 2/2006 | Amplatz |
| 7,033,372 B1 | 4/2006 | Cahalan |
| 7,037,329 B2 | 5/2006 | Martin |
| 7,044,134 B2 | 5/2006 | Khairkhahan et al. |
| 7,097,653 B2 | 8/2006 | Freudenthal et al. |
| 7,105,024 B2 | 9/2006 | Richelsoph |
| 7,159,593 B2 | 1/2007 | McCarthy et al. |
| 7,226,466 B2 | 6/2007 | Opolski |
| 7,317,951 B2 | 1/2008 | Schneider et al. |
| 7,338,514 B2 | 3/2008 | Wahr et al. |
| 7,350,995 B1 | 4/2008 | Rhodes |
| 7,419,498 B2 | 9/2008 | Opolski et al. |
| 7,445,630 B2 | 11/2008 | Lashinski et al. |
| 7,473,266 B2 | 1/2009 | Glaser |
| 7,485,141 B2 | 2/2009 | Majercak et al. |
| 7,524,330 B2 | 4/2009 | Berreklouw |
| 7,530,995 B2 | 5/2009 | Quijano et al. |
| 7,611,534 B2 | 11/2009 | Kapadia et al. |
| 7,625,392 B2 | 12/2009 | Coleman et al. |
| 7,658,747 B2 | 2/2010 | Forde et al. |
| 7,678,123 B2 | 3/2010 | Chanduszko |
| 7,691,144 B2 | 4/2010 | Chang et al. |
| 7,699,297 B2 | 4/2010 | Cicenas et al. |
| 7,704,268 B2 | 4/2010 | Chanduszko |
| 7,722,629 B2 | 5/2010 | Chambers |
| 7,766,966 B2 | 8/2010 | Richelsoph |
| 7,819,890 B2 | 10/2010 | Russo et al. |
| 7,842,026 B2 | 11/2010 | Cahill et al. |
| 7,871,419 B2 | 1/2011 | Devellian et al. |
| 7,905,901 B2 | 3/2011 | Corcoran et al. |
| 7,927,370 B2 | 4/2011 | Webler et al. |
| 7,967,769 B2 | 6/2011 | Faul et al. |
| 7,976,564 B2 | 7/2011 | Blaeser et al. |
| 8,010,186 B1 | 8/2011 | Ryu |
| 8,021,359 B2 | 9/2011 | Auth et al. |
| 8,034,061 B2 | 10/2011 | Amplatz et al. |
| 8,043,360 B2 | 10/2011 | Mcnamara et al. |
| 8,048,147 B2 | 11/2011 | Adams |
| 8,070,708 B2 | 12/2011 | Rottenberg et al. |
| 8,091,556 B2 | 1/2012 | Keren et al. |
| 8,157,860 B2 | 4/2012 | McNamara et al. |
| 8,172,896 B2 | 5/2012 | McNamara et al. |
| 8,252,042 B2 | 8/2012 | McNamara et al. |
| 8,303,623 B2 | 11/2012 | Melzer et al. |
| 8,313,505 B2 | 11/2012 | Amplatz et al. |
| 8,366,088 B2 | 2/2013 | Allen et al. |
| 8,398,670 B2 | 3/2013 | Amplatz et al. |
| 8,460,372 B2 | 6/2013 | McNamara et al. |
| 8,777,974 B2 | 7/2014 | Amplatz et al. |
| 2001/0029368 A1 | 10/2001 | Berube |
| 2002/0029061 A1 | 3/2002 | Amplatz et al. |
| 2002/0062135 A1 | 5/2002 | Mazzocchi et al. |
| 2002/0072765 A1 | 6/2002 | Mazzocchi et al. |
| 2002/0077698 A1 * | 6/2002 | Peredo ..................... 623/2.13 |
| 2002/0082525 A1 | 6/2002 | Oslund et al. |
| 2002/0082613 A1 | 6/2002 | Hathaway et al. |
| 2002/0095172 A1 | 7/2002 | Mazzocchi et al. |
| 2002/0095173 A1 | 7/2002 | Mazzocchi et al. |
| 2002/0143289 A1 | 10/2002 | Ellis et al. |
| 2002/0161424 A1 | 10/2002 | Rapacki et al. |
| 2002/0161432 A1 | 10/2002 | Mazzucco et al. |
| 2002/0165606 A1 | 11/2002 | Wolf et al. |
| 2002/0169377 A1 | 11/2002 | Khairkhahan et al. |
| 2002/0173742 A1 | 11/2002 | Keren et al. |
| 2002/0177894 A1 * | 11/2002 | Acosta et al. ............... 623/1.24 |
| 2002/0183826 A1 | 12/2002 | Dorn et al. |
| 2002/0198563 A1 | 12/2002 | Gainor et al. |
| 2003/0093072 A1 | 5/2003 | Friedman |
| 2003/0125798 A1 | 7/2003 | Martin |
| 2004/0044351 A1 | 3/2004 | Searle |
| 2004/0087937 A1 | 5/2004 | Eggers et al. |
| 2004/0093075 A1 | 5/2004 | Kuehne |
| 2004/0102719 A1 | 5/2004 | Keith et al. |
| 2004/0102797 A1 | 5/2004 | Golden et al. |
| 2004/0111095 A1 | 6/2004 | Gordon et al. |
| 2004/0133236 A1 | 7/2004 | Chanduszko |
| 2004/0143292 A1 | 7/2004 | Marino et al. |
| 2004/0162514 A1 | 8/2004 | Alferness et al. |
| 2004/0176788 A1 | 9/2004 | Opolski |
| 2004/0193261 A1 | 9/2004 | Berreklouw |
| 2004/0206363 A1 | 10/2004 | Mccarthy et al. |
| 2004/0220653 A1 | 11/2004 | Borg et al. |
| 2004/0236308 A1 | 11/2004 | Herweck et al. |
| 2004/0243143 A1 | 12/2004 | Corcoran et al. |
| 2004/0267306 A1 | 12/2004 | Blaeser et al. |

(56) References Cited

U.S. PATENT DOCUMENTS

| | | | |
|---|---|---|---|
| 2005/0015953 A1 | 1/2005 | Keidar | |
| 2005/0049692 A1 | 3/2005 | Numamoto et al. | |
| 2005/0049697 A1 | 3/2005 | Sievers | |
| 2005/0065507 A1 | 3/2005 | Hartley et al. | |
| 2005/0065548 A1 | 3/2005 | Marino et al. | |
| 2005/0065589 A1 | 3/2005 | Schneider et al. | |
| 2005/0070934 A1 | 3/2005 | Tanaka et al. | |
| 2005/0075655 A1 | 4/2005 | Bumbalough et al. | |
| 2005/0080400 A1 | 4/2005 | Corcoran et al. | |
| 2005/0096735 A1* | 5/2005 | Hojeibane et al. | 623/1.24 |
| 2005/0113868 A1 | 5/2005 | Devellian et al. | |
| 2005/0137609 A1 | 6/2005 | Guiraudon | |
| 2005/0137686 A1 | 6/2005 | Salahieh et al. | |
| 2005/0148925 A1 | 7/2005 | Rottenberg et al. | |
| 2005/0165344 A1 | 7/2005 | Dobak, III | |
| 2005/0187616 A1 | 8/2005 | Realyvasquez | |
| 2005/0240205 A1 | 10/2005 | Berg et al. | |
| 2005/0251063 A1 | 11/2005 | Basude | |
| 2005/0251187 A1 | 11/2005 | Beane et al. | |
| 2005/0267523 A1 | 12/2005 | Devellian et al. | |
| 2005/0267524 A1 | 12/2005 | Chanduszko | |
| 2005/0273075 A1 | 12/2005 | Krulevitch et al. | |
| 2005/0288722 A1 | 12/2005 | Eigler et al. | |
| 2006/0004323 A1 | 1/2006 | Chang et al. | |
| 2006/0004434 A1 | 1/2006 | Forde et al. | |
| 2006/0009715 A1 | 1/2006 | Khairkhahan et al. | |
| 2006/0009800 A1 | 1/2006 | Christianson et al. | |
| 2006/0085060 A1 | 4/2006 | Campbell | |
| 2006/0095066 A1 | 5/2006 | Chang et al. | |
| 2006/0122646 A1 | 6/2006 | Corcoran et al. | |
| 2006/0122647 A1 | 6/2006 | Callaghan et al. | |
| 2006/0135990 A1 | 6/2006 | Johnson | |
| 2006/0136043 A1 | 6/2006 | Cully et al. | |
| 2006/0155305 A1 | 7/2006 | Freudenthal et al. | |
| 2006/0184088 A1 | 8/2006 | Van Bibber et al. | |
| 2006/0210605 A1 | 9/2006 | Chang et al. | |
| 2006/0241745 A1 | 10/2006 | Solem | |
| 2006/0247680 A1 | 11/2006 | Amplatz et al. | |
| 2006/0253184 A1 | 11/2006 | Amplatz | |
| 2006/0259121 A1 | 11/2006 | Osypka | |
| 2006/0276882 A1* | 12/2006 | Case et al. | 623/1.24 |
| 2007/0016250 A1 | 1/2007 | Blaeser et al. | |
| 2007/0021739 A1 | 1/2007 | Weber | |
| 2007/0027528 A1* | 2/2007 | Agnew | 623/1.24 |
| 2007/0038295 A1* | 2/2007 | Case et al. | 623/2.18 |
| 2007/0043431 A1 | 2/2007 | Melsheimer | |
| 2007/0088388 A1 | 4/2007 | Opolski et al. | |
| 2007/0118207 A1 | 5/2007 | Amplatz et al. | |
| 2007/0123934 A1 | 5/2007 | Whisenant et al. | |
| 2007/0129755 A1 | 6/2007 | Abbott et al. | |
| 2007/0168018 A1 | 7/2007 | Amplatz et al. | |
| 2007/0168019 A1 | 7/2007 | Amplatz et al. | |
| 2007/0185513 A1 | 8/2007 | Woolfson et al. | |
| 2007/0197952 A1 | 8/2007 | Stiger | |
| 2007/0198060 A1 | 8/2007 | Devellian et al. | |
| 2007/0209957 A1 | 9/2007 | Glenn et al. | |
| 2007/0225759 A1 | 9/2007 | Thommen et al. | |
| 2007/0265658 A1 | 11/2007 | Nelson et al. | |
| 2007/0270741 A1 | 11/2007 | Hassett et al. | |
| 2007/0282157 A1 | 12/2007 | Rottenberg et al. | |
| 2008/0015619 A1 | 1/2008 | Figulla et al. | |
| 2008/0033425 A1 | 2/2008 | Davis et al. | |
| 2008/0033543 A1 | 2/2008 | Gurskis et al. | |
| 2008/0039804 A1 | 2/2008 | Edmiston et al. | |
| 2008/0039922 A1 | 2/2008 | Miles et al. | |
| 2008/0058940 A1 | 3/2008 | Wu et al. | |
| 2008/0071135 A1 | 3/2008 | Shaknovich | |
| 2008/0086168 A1 | 4/2008 | Cahill | |
| 2008/0103508 A1 | 5/2008 | Karakurum | |
| 2008/0119891 A1 | 5/2008 | Miles et al. | |
| 2008/0125861 A1 | 5/2008 | Webler et al. | |
| 2008/0154250 A1 | 6/2008 | Makower et al. | |
| 2008/0154302 A1 | 6/2008 | Opolski et al. | |
| 2008/0154351 A1 | 6/2008 | Leewood et al. | |
| 2008/0154355 A1 | 6/2008 | Benichou et al. | |
| 2008/0161901 A1 | 7/2008 | Heuser et al. | |
| 2008/0172123 A1 | 7/2008 | Yadin | |
| 2008/0177381 A1 | 7/2008 | Navia et al. | |
| 2008/0183279 A1* | 7/2008 | Bailey et al. | 623/1.24 |
| 2008/0188888 A1 | 8/2008 | Adams et al. | |
| 2008/0215008 A1 | 9/2008 | Nance et al. | |
| 2008/0228264 A1 | 9/2008 | Li et al. | |
| 2008/0249397 A1 | 10/2008 | Kapadia | |
| 2008/0249612 A1* | 10/2008 | Osborne et al. | 623/1.24 |
| 2008/0262592 A1 | 10/2008 | Jordan et al. | |
| 2008/0269662 A1 | 10/2008 | Vassiliades et al. | |
| 2008/0312679 A1 | 12/2008 | Hardert et al. | |
| 2009/0018562 A1 | 1/2009 | Amplatz et al. | |
| 2009/0018570 A1 | 1/2009 | Righini et al. | |
| 2009/0025820 A1 | 1/2009 | Adams | |
| 2009/0030495 A1 | 1/2009 | Koch | |
| 2009/0054984 A1 | 2/2009 | Shortkroff et al. | |
| 2009/0062841 A1 | 3/2009 | Amplatz et al. | |
| 2009/0082803 A1 | 3/2009 | Adams et al. | |
| 2009/0099647 A1 | 4/2009 | Glimsdale et al. | |
| 2009/0112050 A1 | 4/2009 | Farnan et al. | |
| 2009/0112244 A1 | 4/2009 | Freudenthal | |
| 2009/0112251 A1 | 4/2009 | Qian et al. | |
| 2009/0131978 A1 | 5/2009 | Gainor et al. | |
| 2009/0171386 A1 | 7/2009 | Amplatz et al. | |
| 2009/0177269 A1* | 7/2009 | Kalmann et al. | 623/1.24 |
| 2009/0187214 A1 | 7/2009 | Amplatz et al. | |
| 2009/0209855 A1 | 8/2009 | Drilling et al. | |
| 2009/0209999 A1 | 8/2009 | Afremov | |
| 2009/0210047 A1 | 8/2009 | Amplatz et al. | |
| 2009/0210048 A1 | 8/2009 | Amplatz et al. | |
| 2009/0234443 A1 | 9/2009 | Ottma et al. | |
| 2009/0264991 A1 | 10/2009 | Paul, Jr. et al. | |
| 2009/0270840 A1 | 10/2009 | Miles et al. | |
| 2009/0270909 A1 | 10/2009 | Oslund et al. | |
| 2010/0022940 A1 | 1/2010 | Thompson | |
| 2010/0023046 A1 | 1/2010 | Heidner et al. | |
| 2010/0023048 A1 | 1/2010 | Mach | |
| 2010/0023121 A1 | 1/2010 | Evdokimov et al. | |
| 2010/0030259 A1 | 2/2010 | Pavcnik et al. | |
| 2010/0030321 A1 | 2/2010 | Mach | |
| 2010/0049307 A1 | 2/2010 | Ren | |
| 2010/0051886 A1 | 3/2010 | Cooke et al. | |
| 2010/0057192 A1 | 3/2010 | Celermajer | |
| 2010/0063578 A1 | 3/2010 | Ren et al. | |
| 2010/0094335 A1 | 4/2010 | Gerberding et al. | |
| 2010/0106235 A1 | 4/2010 | Kariniemi et al. | |
| 2010/0121370 A1 | 5/2010 | Kariniemi | |
| 2010/0131053 A1* | 5/2010 | Agnew | 623/2.13 |
| 2010/0179491 A1 | 7/2010 | Adams et al. | |
| 2010/0211046 A1 | 8/2010 | Adams et al. | |
| 2010/0234881 A1 | 9/2010 | Blaeser et al. | |
| 2010/0249490 A1 | 9/2010 | Farnan | |
| 2010/0249491 A1 | 9/2010 | Farnan et al. | |
| 2010/0249909 A1 | 9/2010 | McNamara et al. | |
| 2010/0249910 A1 | 9/2010 | McNamara et al. | |
| 2010/0256548 A1 | 10/2010 | McNamara et al. | |
| 2010/0256753 A1 | 10/2010 | McNamara | |
| 2010/0268316 A1 | 10/2010 | Brenneman et al. | |
| 2010/0274351 A1 | 10/2010 | Rolando et al. | |
| 2010/0298755 A1 | 11/2010 | McNamara et al. | |
| 2010/0305685 A1 | 12/2010 | Millwee et al. | |
| 2010/0324588 A1 | 12/2010 | Miles et al. | |
| 2011/0004239 A1 | 1/2011 | Russo et al. | |
| 2011/0004296 A1 | 1/2011 | Lutter et al. | |
| 2011/0022079 A1 | 1/2011 | Miles et al. | |
| 2011/0071623 A1 | 3/2011 | Finch et al. | |
| 2011/0071624 A1 | 3/2011 | Finch et al. | |
| 2011/0087261 A1 | 4/2011 | Wittkampf et al. | |
| 2011/0093062 A1 | 4/2011 | Cartledge et al. | |
| 2011/0106149 A1 | 5/2011 | Ryan et al. | |
| 2011/0112633 A1 | 5/2011 | Devellian et al. | |
| 2011/0130784 A1 | 6/2011 | Kusleika | |
| 2011/0184439 A1 | 7/2011 | Anderson et al. | |
| 2011/0213364 A1 | 9/2011 | Davis et al. | |
| 2011/0218477 A1 | 9/2011 | Keren et al. | |
| 2011/0218478 A1 | 9/2011 | Keren et al. | |
| 2011/0218479 A1 | 9/2011 | Rottenberg et al. | |
| 2011/0218480 A1 | 9/2011 | Rottenberg et al. | |

(56) References Cited

U.S. PATENT DOCUMENTS

| | | |
|---|---|---|
| 2011/0218481 A1 | 9/2011 | Rottenberg |
| 2011/0257723 A1 | 10/2011 | Mcnamara |
| 2011/0270239 A1 | 11/2011 | Werneth |
| 2011/0283871 A1 | 11/2011 | Adams |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0307000 A1 | 12/2011 | Amplatz et al. |
| 2011/0319989 A1 | 12/2011 | Lane et al. |
| 2012/0022427 A1 | 1/2012 | Kapadia |
| 2012/0053686 A1 | 3/2012 | Mcnamara et al. |
| 2012/0130301 A1 | 5/2012 | Mcnamara et al. |
| 2012/0165928 A1 | 6/2012 | Nitzan et al. |
| 2012/0259263 A1 | 10/2012 | Celermajer et al. |
| 2012/0265296 A1 | 10/2012 | Mcnamara et al. |
| 2012/0289882 A1 | 11/2012 | Mcnamara et al. |
| 2012/0290062 A1 | 11/2012 | Mcnamara et al. |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0204175 A1 | 8/2013 | Sugimoto |
| 2013/0231737 A1 | 9/2013 | McNamara et al. |
| 2013/0267885 A1 | 10/2013 | Celermajer et al. |
| 2014/0012368 A1 | 1/2014 | Sugimoto et al. |
| 2014/0194971 A1 | 7/2014 | McNamara |
| 2014/0257167 A1 | 9/2014 | Celermajer et al. |
| 2014/0277054 A1 | 9/2014 | McNamara et al. |
| 2015/0039084 A1 | 2/2015 | Levi et al. |
| 2015/0119796 A1 | 4/2015 | Finch |

FOREIGN PATENT DOCUMENTS

| | | |
|---|---|---|
| CN | 1556719 A | 12/2004 |
| CN | 1582136 A | 2/2005 |
| CN | 1780589 A | 5/2006 |
| CN | 101035481 A | 9/2007 |
| CN | 101035488 A | 9/2007 |
| CN | 101292889 A | 10/2008 |
| CN | 101426431 A | 5/2009 |
| CN | 101579267 A | 11/2009 |
| EP | 1264582 A2 | 2/2002 |
| EP | 1470785 A1 | 10/2004 |
| EP | 1849440 A1 | 10/2007 |
| JP | 58-27935 U | 6/1983 |
| JP | 2003530143 | 10/2003 |
| WO | 9527448 A1 | 10/1995 |
| WO | WO98/08456 A1 | 3/1998 |
| WO | WO98/42403 A1 | 10/1998 |
| WO | WO2004/019811 A2 | 3/2004 |
| WO | WO2005/048881 A1 | 6/2005 |
| WO | WO2005/048883 A1 | 6/2005 |
| WO | WO2006/127765 A1 | 11/2006 |
| WO | 2008/058940 | 5/2008 |
| WO | 2008055301 A1 | 5/2008 |
| WO | 2010111666 A1 | 9/2010 |
| WO | 2010128501 A1 | 11/2010 |
| WO | 2010129089 A2 | 11/2010 |
| WO | WO2010/129511 A2 | 11/2010 |
| WO | 2011093941 A2 | 8/2011 |
| WO | 2011094521 A2 | 8/2011 |
| WO | 2011093941 A3 | 10/2011 |
| WO | 2011093941 A4 | 12/2011 |
| WO | 2011094521 A3 | 12/2011 |
| WO | 2012071075 A1 | 5/2012 |
| WO | 2012109557 A2 | 8/2012 |
| WO | 2012109557 A3 | 1/2013 |
| WO | 2013096965 A1 | 6/2013 |

OTHER PUBLICATIONS

Nanotechnology in Prosthetic Heart Valves, Steven R. Bailey, MD, approx. date 2005, presentation, 31 pages.

A Philosophical Approach to Mitral Valve Repair, Vincent A. Gaudiani, MD and Audrey L. Fisher, MPH, Apr. 24, 2009, presentation, 28 pages.

Direct Flow Medical—My Valve is Better, Steven F. Bolling, MD, Apr. 23, 2009, presentation, 21 pages.

No! Valve Replacement: Patient Prosthetic Mismatch Rarely Occurs, Joseph S. Coselli, MD, Apr. 25, 2009, presentation, 75 pages.

Transcatheter Aortic Valve Therapy: Summary Thoughts, Martin B. Leon, MD, Jun. 24, 2009, presentation, 19 pages.

The Good, the Bad and the Ugly of Transcatheter AVR, Jeffrey W. Moses, MD, Jul. 10, 2009, presentation, 28 pages.

Valve Implantation, Ziyad M. Hijazi, MD, May 10, 2007, presentation, 36 pages.

Transcatheter Devices for Mitral Valve Repair, Surveying the Landscape, Gregg W. Stone, MD, Jul. 10, 2009, presentation, 48 pages.

Comparative Study of in vitro Flow Characteristics between a Human Aortic Valve and a Designed Aortic Valve and Six Corresponding Types of Prosthetic Heart Valves, B. Stormer et al., Eur. Surg. Res. 8: 117-131 (1976), 15 pages.

The Use of an Artificial Foraminal Valve Prosthesis in the Closure of Interatrial and Interventricular Septal Defects, Ramon Larios et al., Dis. Chest. 1959: 36; 631-41, 12 pages.

Insertion of a Fenestrated Amplatzer Atrial Sestosotomy Device for Severe Pulmonary Hypertension, A.J. O'Loughlin et al., Heart Lung Circ. 2006, 15(4):275-77, 3 pages.

Long-Term Follow up of a Fenestrated Amplatzer Atrial Septal Occluder in Pulmonary Arterial Hypertension, T.F. Althoff, et al., Chest 2008, 133:183-85, 5 pages.

International Searching Authority; International Search Report and Written Opinion, PCTUS2010/026574, Mailed Nov. 19, 2010, 9 pages.

International Searching Authority; International Search Report and Written Opinion; PCT/US10//58110; Mailed Aug. 26, 2011; 14 pgs.

Related Application No. PCT/US11/22895.
Related U.S. Appl. No. 12/719,833.
Related U.S. Appl. No. 12/719,834.
Related U.S. Appl. No. 12/719,840.
Related U.S. Appl. No. 12/719,843.
Related U.S. Appl. No. 12/848,084.
Related Application No. PCT/US10/26574.
Related U.S. Appl. No. 12/954,468.
Related U.S. Appl. No. 12/954,521.
Related U.S. Appl. No. 12/954,555.
Related U.S. Appl. No. 12/954,529.
Related U.S. Appl. No. 12/954,537.
Related U.S. Appl. No. 12/954,541.
Related Application No. PCT/US10/58110.
Related U.S. Appl. No. 13/167,502.
Related U.S. Appl. No. 13/016,290.

International Search Report and Written Opinion; PCT/US11/22895; mailed Oct. 24, 2011; 14 pgs.

Blade atrial septostomy: collaborative study, SC Park et al, Circulation, 1982, 66:258-266, 10 pages.

Ventriculofemoroatrial shunt: a viable alternative for the treatment of hydrocephalus, Matthew F. Philips, M.D., et al, J Neurosurg 86:1063-1066, 1997, 4 pages.

A One-Way Valved Atrial Septal Patch: A New Surgical Technique and Its Clinical Application, N. Ad, MD et al, The Journal of Thoracic and Cardiovascular Surgery, Apr. 1996, vol. 111:841-848, 8 pages.

Very Small Pulmonary Arteries: Central End-to-Side Shunt, Kevin G. Watterson, et al, Ann Thorac Surg, 1991; 52:1132-1138, 6 pages.

Stent Implantation to Create Interatrial Communications in Patients With Complex Congenital Heart Disease, Carlos A. C. Pedra, MD, et al, Catheterization and Cardiovascular Interventions 47:310-313 (1999), 4 pages.

Creation and Maintenance of an Adequate Interatrial Communicationin left Atrioventricular Valve Atresia or Stenosis, Stanton B. Perry, MD, et al, The American Journal of Cardiology, 1986; 58: 622-626, 5 pages.

PCT/US12/024680, International Application Serial No. PCT/US12/024680, International Preliminary Report on Patentability and Written Opinion mailed Aug. 22, 2013, DC Devices, Inc, 7 pages.

(56) References Cited

OTHER PUBLICATIONS 10772411.4, ,"European Application Serial No. 10772411, European Search Opinion and Supplementary European Search Report mailed Mar. 16, 2012", 5 pages.

Atz, Andrew M. et al., "Preoperative Management of Pulmonary Venous Hypertension in Hypoplastic Left Heart Syndrome With Restrictive Atrial Septal Defect", The American Journal of Cardiology, vol. 83, Apr. 15, 1999, pp. 1224-1228.

Cheatham, John P., "Intervention in the critically ill neonate and infant with hypoplastic left heart syndrome and intact atrial septum", Journal of Interventional Cardiology, vol. 14, No. 3, 2001, pp. 357-366.

Design News, ,"Low Power Piezo Motion", http://www.designnews.com/document.asp?doc_id=229053&dfpPParams&dfpPParams=ht_13,aid_229053&dfpLayout=article, May 14, 2010, 3 pages.

EP12180631.9, ,"European Application Serial No. EP12180631.9, European Search Report mailed Nov. 19, 2012", 5 pages.

Merchant, Faisal M. et al., "Advances in Arrhythmia and Electrophysiology; Implantable Sensors for Heart Failure", Circ. Arrhythm. Electrophysiol., vol. 3, Dec. 2010,pp. 657-667.

PCT/AU2007/01704, "International Application Serial No. PCT/AU2007/01704, International Preliminary Report on Patentability mailed Aug. 22, 2008", Aug. 22, 2008, 5 pages.

PCT/AU2007/01704, "International Application Serial No. PCT/AU2007/01704, Written Opinion mailed Jan. 16, 2008", Aug. 16, 2008, 5 pages.

PCT/US10/58110, "International Application Serial No. PCT/US10/58110, International Preliminary Report on Patentability mailed Nov. 27, 2012", DC Devices, Inc., 11 pages.

PCT/US2010/026574, "International Application Serial No. PCT/US2010/026574, International Preliminary Report on Patentability mailed Nov. 10, 2011", Nov. 10, 2011, 7 pages.

PCT/US2011/041841, "International Application Serial No. PCT/US2011/041841, International Preliminary Report on Patentability and Written Opinion mailed Jun. 6, 2013", 8 pages.

PCT/US2011/041841, "International Application Serial No. PCT/US2011/041841, International Search Report and Written Opinion mailed Feb. 9, 2012", Feb. 9, 2012, 12 pages.

PCT/US2012/024680, "International Application Serial No. PCT/US2012/024680, International Search Report and Written Opinion mailed Oct. 23, 2012", 11 pages.

PCT/US2012/071588, "International Application Serial No. PCT/US2012/071588, International Search Report and Written Opinion mailed Apr. 19, 2013", 19 pages.

Sommer, et al., "Transcatheter Creation of Atrial Septal Defect and Fontan Fenestration with "Butterfly" Stent Technique", Supplement to Journal of the American College of Cardiology, V. 33, No. 2, Supplement A, Feb. 1999, 3 pages.

McMahon, Jim; Piezo motors and actuators: Streamlining medical device performance; Designfax; Mar. 23, 2010; 5 pgs.; retrieved from the internet on Jul. 19, 2012 (http://www.designfax.net/enews/20100323/feature-1.asp).

Park et al.; Blade atrial septostomy: Collaborative study; Circulation; 66(2); pp. 258-266; Aug. 1982.

Physik Instrumente; Piezo for Motion Control in Medical Design and Drug Research (product information); Physik Instrumente (PI) GmbH & Co. KG; 22 pgs.; © Nov. 21, 2010.

Roven et al.; Effect of compromising right ventricular function in left ventricular failure by means of interatrial and other shunts; Am J Cardiol.; 24(2); pp. 209-219; Aug. 1969.

Sambhi et al.; Pathologic Physiology of Lutembacher Syndrome; Am J Cardiol.; 2(6); pp. 681-686; Dec. 1958.

Webber, Ralph; Piezo Motor Based Medical Devices; Medical Design Technology; 5 pgs.; Apr. 2, 2009; retrieved from the internet on Jul. 19, 2012 (http://mdtmag.com/articles/2009/04/piezo-motor-based-medical-devices).

Forcucci et al.; U.S. Appl. No. 14/807,544 entitled "Devices and methods for treating heart failure," filed Jul. 23, 2015.

Finch; U.S. Appl. No. 14/645,416 entitled "Devices and methods for treating heart failure," filed Mar. 11, 2015.

Celermajer et al.; U.S. Appl. No. 14/498,903 entitled "Apparatus and methods to create and maintain an intra-atrial pressure relief opening," filed Sep. 26, 2014.

McNamara et al.; U.S. Appl. No. 14/612,022 entitled "Methods and devices for intra-atrial shunts having adjustable sizes," filed Feb. 2, 2015.

\* cited by examiner

FIG. 8

DEVICES AND METHODS FOR REDUCING VENOUS PRESSURE

CLAIM TO PRIORITY

This application claims priority from, and the benefits of 35 U.S.C. §119 applicable to, U.S. Provisional Application 61/299,656, filed Jan. 29, 2010, the contents of which are herein incorporated by reference in their entirety.

FIELD

The present disclosure relates to methods and devices for treating heart failure. More specifically, the present invention relates to methods and devices for reducing venous pressure and treating symptoms of elevated venous pressures.

BACKGROUND

Heart failure is a condition effecting millions of people worldwide. Heart failure includes failure of either the left side of the heart, the right side of the heart, or both. Right heart failure can lead to elevated right atrial pressures, and the elevated right atrial pressures in turn can lead to serious clinical conditions, including impaired renal function. More specifically, right heart failure can lead to elevated renal vein pressures, which in turn may cause additional adverse conditions in the body. There exists a need to percutaneously treat the symptoms of right heart failure by preventing the elevated pressure from harming key vessels and organs in the body.

A few techniques have been disclosed as a means of treating right heart failure. U.S. Pat. No. 7,159,593 issued to Quijano et al. discloses a pair of stented valves. One valve sits at the right atrium (RA)/Inferior Vena Cava (IVC) junction, while the second stented valve is implanted at the RA/Superior Vena Cava (SVC) junction. Such an approach suffers from deficiencies. The foremost problem with such approach is that no consideration is given to the effect that implanting a valve in both the SVC and IVC would have on the blood pressure in RA and coronary sinus. With both the upper and lower body blocked off by stented valves, the blood pressure in the RA would climb dramatically, causing the RA to balloon to a hazardous size. The second major problem with the approach disclosed in Quijano et al. is the anatomical difficulties related to implanting a stented valve at the junction of the IVC and the RA. The RA/IVC junction is often flared (the IVC diameter increases from lower to upper part) and has an asymmetrical conical shape which does not lend itself well to a tubular implant. Additionally, the anatomical differences from person to person in this area would make designing a stented valve for a large population impractical. For example, the angle of the IVC to the RA can vary dramatically from person to person, and may also change as heart disease progresses. Still further, there may or may not be a Eustachian valve at the RA/IVC junction, depending on the individual anatomy. This valve could interfere with device deployment, safety and/or function. Finally, Quijano et al. do not address the problem of accidental hepatic vein occlusion by the device in question. The hepatic veins reside just below the RA/IVC junction, and their location is highly variable. Occasionally the hepatic veins empty out into the IVC in the immediate vicinity of the junction with the RA. Based on these errors and omissions, it seems clear that there still exists a need for a reliable means of treating right heart failure and elevated venous pressures.

U.S. Pat. No. 7,350,995 to Quijano et al. discloses a pair of stented tissue valves which are connected by means of various connecting members. This disclosure suffers from all of the above-mentioned deficiencies, and does not address any of the above physiological problems associated with implanting valves in both the SVC and the IVC. Therefore there still exists a need for a reliable means of treating right heart failure and elevated venous pressures.

U.S. patent application Publ. No. 2005/0049692 by Numamoto et al. discloses the use of a stented valve to treat right heart failure. The valve may be placed in the SVC or the IVC. The inventors teach that the IVC valve should be placed in the vicinity of the junction between the IVC and the RA. They also teach that the device should be placed above the hepatic veins. This disclosure fails to address the problems associated with varying anatomies and the difficult geometry of the RA/IVC junction. The disclosure also does not address the problem of accidental occlusion of the hepatic veins. Additionally, the inventors do not disclose a means of preventing excessive blood pressures from building up in the upper body. Therefore, there still exists a need for a reliable means of treating right heart failure by safely controlling elevated venous pressures.

SUMMARY

In general, the present disclosure covers devices and methods to treat heart failure by reducing venous pressure. To this end, methods and devices are disclosed herein which include implantation of a pressure reduction device into the inferior vena cava, in order to reduce the venous pressure in the lower IVC and renal veins.

In one exemplary embodiment, a pressure reduction device includes an elongate stent member and a valve device. The valve apparatus is fixed to the elongate stent member by an attachment means. The valve features a leaflet or plurality of leaflets, which are configured to open up the valve when the lower IVC pressure is greater than the upper IVC blood pressure. This occurs primarily during inspiration, as the lungs fill up with air and the intrathoracic pressure drops, drawing blood into the RA. Body position also plays a role in the above-mentioned situation because IVC pressure is higher when standing than lying. The valve leaflets are also configured to close when the RA and upper IVC pressure rises back to a level that is greater than the lower IVC pressure. The valve therefore prevents the elevated RA blood pressure, caused by heart failure, from reaching the lower IVC, including the renal veins. The blood which would have been forced into the lower IVC is instead redirected to the SVC, the RA, and the coronary sinus.

In embodiments, the pressure control device which includes an elongate stent member and a valve is placed in the IVC below the hepatic veins and above the renal veins. The pressure reduction device further includes an emergency pressure relief feature mechanism which allows blood to flow retrograde through the pressure reduction device in the event that the upper venous pressures escalate to dangerous levels. This protects the upper body, SVC, and RA from prolonged exposure to overly high venous pressures. In this way the pressure control device controls both the upper and lower venous pressures by keeping both pressures within the bounds of what may be considered acceptable for the patient.

In embodiments, the pressure control device includes an elongate tubular stent member and at least one pressure control feature. The pressure control feature is configured such that when blood is flowing from the region of the IVC above the device to the region of the IVC below the device the pressure is reduced by hydrodynamic means. In this way the lower venous pressure is reduced without complete occlusion of the vein and without complete prohibition of blood flow through the device. The pressure control device may further be configured such that when blood is flowing normally from the lower body to the upper body the general amount of pressure reduction or pressure drop across the device is decreased. This would allow for normal blood flow when blood is flowing normally into the RA and would allow for reduced blood flow when the upper IVC pressure is greater than the lower IVC pressure. Additionally, the pressure control feature may take advantage of the physiological changes that occur during inspiration and/or body position to further open the lumen of the device and allow for increased blood flow into the RA from the IVC.

In still another alternative embodiment the pressure control device includes an elongate stent member and a combination of valves and other pressure control features. Other pressure control features include conic shaped membranes, or hemodynamic tortuous paths, or other means of creating a pressure differential or drop across the length of the pressure control device.

In an additional embodiment, a method is disclosed for treating heart failure by implanting the herein-described pressure control device into the IVC. The method includes positioning the implant, and deploying the implant in the appropriate location using a suitable delivery device.

In one embodiment, a device is used for treating heart failure of a patient. The device includes a stent for implantation in an inferior vena cava of the patient, at least one pressure control feature attached to the stent, and at least one connector joining the at least one pressure control feature to said stent, wherein the pressure control feature is configured to prevent elevated blood pressure from damaging an organ or vessel.

In another embodiment, a device is used for treating heart failure of a patient. The device includes an elongate tubular stent member, at least one pressure control feature, at least one pressure relief feature, and a connector or connector means joining said at least one pressure control feature to said elongate tubular member, wherein the at least one pressure control feature is configured to prevent elevated blood pressure from damaging an organ or a vessel by inducing a pressure differential across the device, and wherein the pressure relief feature is configured to reduce the pressure differential if the pressure differential exceeds a desired value.

In another embodiment, the device is used to reduce venous pressure. The device includes a stent adapted to exert an outward radial force upon a lumen of an inferior vena cava, at least one anchor integral with said stent adapted to contact a surface of said lumen, a valve having a first side and a second side and configured to allow blood to flow in a first direction, wherein said first direction is a normal direction of blood flow and wherein said normal direction of blood flow is from said first side to said second side, said valve configured to close when a venous pressure on the second side of the valve exceeds a venous pressure on the first side of the valve by a predetermined amount, and an emergency release feature that allows blood to flow retrograde in a direction opposite to the normal direction while said valve is at least partially closed.

In yet another embodiment, the device is useful for reducing venous pressure. The device includes a stent adapted to exert an outward radial force upon a lumen of an inferior vena cava, a pressure control device attached to said stent, said pressure control device having a first opening and a second opening, said second opening having an area larger than said first opening, and a biocompatible sheet having a first side and a second side and secured to said pressure control device, said sheet comprising apertures configured to open when venous pressures on the first side and second side of the biocompatible sheet are normal, thereby allowing blood flow in a first direction and for said apertures to close when the venous pressure on the second side exceeds the venous pressure on the first side by a predetermined amount, thereby impeding blood flow in the first direction.

In yet another embodiment, the disclosure includes a method of reducing venous pressure. The method includes step of providing a pressure control device comprising a valve configured to allow blood to flow in a normal direction in an inferior vena cava and implanting the pressure control device into a patient's inferior vena cava between said patient's hepatic veins and renal veins, wherein the pressure control device is configured to close when a venous pressure downstream from the valve exceeds a venous pressure upstream from the valve by a first predetermined amount.

DETAILED DESCRIPTION

Reference will be made to various figures in order to describe the devices and methods for treating heart failure. These methods and devices are particularly useful for treating symptoms of right heart failure by controlling venous pressure and preventing elevated pressures from causing further harm to the body. Specific details are disclosed which would allow one with ordinary skill in the art to make and use the devices and methods disclosed herein. It should be understood that various substitutions and additions can be made by those with ordinary skill in the art while still falling within the inventive features disclosed herein.

Figure 1:
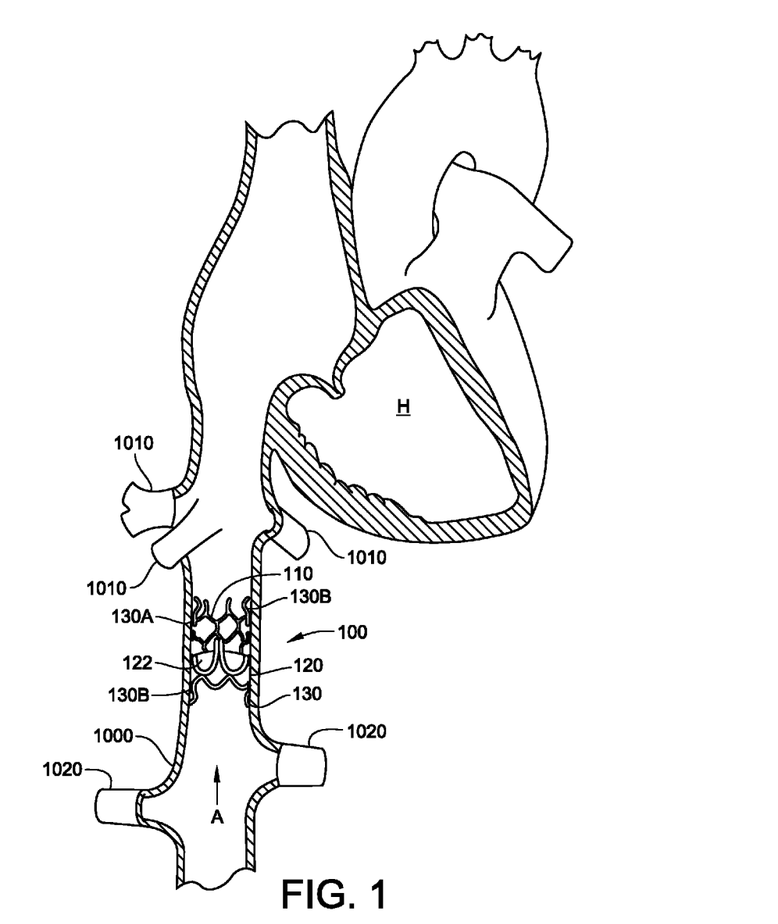
FIG. 1 depicts a first embodiment of a device for reducing venous pressure.

Referring now to FIG. 1, one embodiment of the present invention is depicted. FIG. 1 depicts an illustrative pressure control device 100 deployed in an inferior vena cava (IVC) 1000 of a person between the hepatic veins 1010 and the renal veins 1020. The pressure control device 100 includes an elongate stent member 110 and a pressure control valve 120. The elongate stent member 110 is configured to exert an outward radial pressure on the internal lumen of the IVC, preventing the device from migrating within the IVC.

A series of fixating anchor members 130A-130D are depicted and may be used to further fixate the pressure control device 100 within the IVC. The anchor elements 130A-130D may take the form of short curved struts, as depicted in FIG. 1. The anchors may also be small barbs or hooks that will anchor the stent to an internal wall of a body lumen, such as an inferior vena cave. The stent body comprises struts joined to one another at apices, as better seen in FIG. 2. In this embodiment, anchor elements are depicted on both the upper and lower ends of the device. In other embodiments, however, the anchors may be located on either the upper or lower side of the device, or they may be included throughout the length of the stent member. The valve member may be equipped with a single leaflet, two leaflets or other suitable number of leaflets, such as three or more.

During normal operation, blood flows in the direction of arrow A, from the veins of the patient, through the flow control device 100 to the heart H of the patient. During normal operation, the leaflet or leaflets are open to allow normal blood flow. Thus, during normal operation, blood flows from the renal veins 1020, which are upstream of the pressure control device 100, through the pressure control device. Downstream of the pressure control device, blood from the renal veins joins blood flow from the hepatic veins 1010 for further normal flow to the heart H of the patient. It follows that the pressure upstream of the flow control device is higher than pressure downstream of the pressure control device. Blood pressure in the right atrium of the heart is lower than pressure in the IVC generally and in particular, blood pressure in the right atrium of the heart is lower than blood pressure in the IVC near its juncture with the renal veins.

The pressure control valve 120 of FIG. 1 is configured such that the leaflets are closed and the orifice of the pressure control device is sealed when the pressure above the device in FIG. 1 (that is, downstream of the device and nearer the patient's heart) is greater than the pressure below the device (that is, upstream of the device). The leaflets are normally open and the pressure downstream of the device is normally lower than the pressure upstream of the device, for example, during normal conditions for the patient. The arrow depicts the direction of flow allowed by the valve. In embodiments, the valve is configured to close only when the pressure in or near the heart, that is, downstream of the device, is greater than the pressure upstream or below the device by a selected amount. In one embodiment, the selected amount can equal about 1 to 10 mm Hg for a first closing movement. In one embodiment, a pressure difference required for substantial closing may range from 10 to 25 mm Hg.

The elongate stent member 110 depicted in FIG. 1 may be made of stainless steel, nitinol, titanium, cobalt alloys, cobalt-chromium-nickel alloys, MP35N, a polymeric material, or any other suitable biocompatible material. The stent member may be designed to be self-expanding, balloon expanding, or shape-memory phase-change expanding. The stent member may be made from tubing by means of laser cutting the tube to leave a strut pattern behind. Alternatively, the stent member may be manufactured by wire braiding or wire knitting. Methods of making and deploying a stent member are well known in the art. The thickness of the walls or the wire used to construct a cage may range from about 0.003 to 0.010 inches (about 0.08 to 0.25 mm). Other embodiments may use other thicknesses.

The pressure control valve 120 shown in the illustrative embodiment of FIG. 1 may be a tissue valve or a mechanical check-valve. The tissue valve leaflets may be made of mammalian pericardium, including bovine, ovine, porcine, or equine pericardium. The tissue valve may be chemically treated with various chemical treating agents, such as those well known in the art, including glutaraldehyde, formaldehyde, dialdehyde starch, epoxy, genipin, or a mixture of the above chemical compounds. These various chemical treatments may be used in order to fixate the pericardium, to preserve the structure and function of the tissue valves, or to prevent the buildup of calcium deposits on the tissue valves. Chemical treatments for implantable tissue valves are well known in the art. In another embodiment, the tissue valve may be a venous valve including a mammalian jugular vein. In another embodiment, the tissue valve could be a porcine heart valve, such as a porcine aortic valve. In other embodiments, the valve flaps may be made of elastomeric materials, such as silicone or perfluorocarbon elastomers. In one embodiment, the leaflets are from about 0.5 mm to about 1 mm thick (about 0.02 to about 0.04 inches thick).

The pressure control valve 120 is attached to the stent member 110 by an attachment means or connector 122. The connector 122 may include sutures for attaching the valve members or valve flaps to the struts of the stent, or for suturing the valve to attachment features cut into the stent structure specifically for attachment purposes. Additionally, the tissue valve may be attached by mechanical crimps, or by other connectors.

Figure 2:
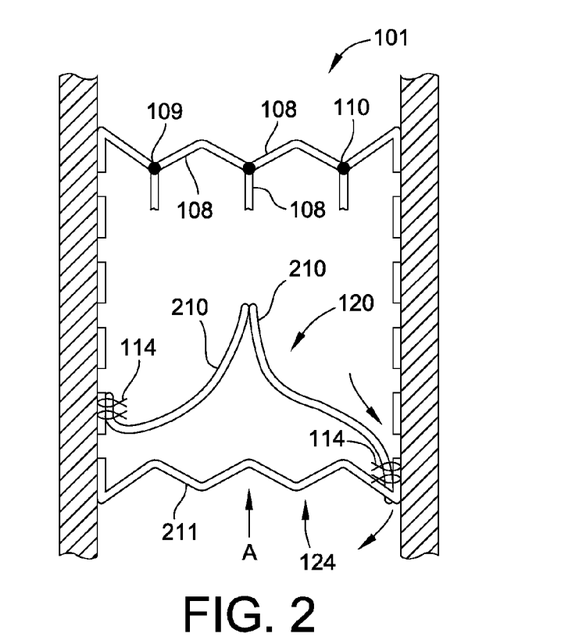
FIG. 2 depicts a second embodiment of a pressure-reducing device.

Referring now to FIG. 2, another embodiment of the present invention is depicted. FIG. 2 shows a simplified cross-section of a pressure control device 101 comprising an integrated emergency pressure relief feature 124. The pressure control device has been simplified for ease of illustration only. The pressure control device 101 depicted in FIG. 2 may be positioned in the same location as disclosed above with reference to FIG. 1, and may be made of any of the above-mentioned materials. In this embodiment, the pressure control device 100 includes a pressure control valve 120 with a plurality of leaflets, such as two or three leaflets. The valve is sewn to an elongate stent structure 110, which supports the pressure control device in the IVC. Anchoring members are not shown here, although anchor members similar to the ones discussed above may be used. The elongate stent structure 110 is primarily composed of short stent struts 108 joined at apices 109. The direction of normal blood flow is shown by arrow A. The smaller arrows show the direction of blood flow in the opposite direction when the emergency pressure relief feature 124 is activated.

In embodiments, the emergency pressure relief feature 124 is a section of the stent wall (as depicted below in later drawings) which has been designed to collapse inward when subjected to a force directed radially outward. The radially outward force is supplied by the blood pressure and the shape and design of the leaflet(s) 211.

As shown in FIG. 2, the leaflets 210 are attached to the stent wall so that as the upper IVC pressure increases, the pressure differential is translated into a force directed radially outward. Leaflet 211, however, is attached to the stent member such that the force generated by the pressure differential across the device is translated to the stent wall as a force directed radially inward. The stent wall may then be designed such that if the pressure differential between upper IVC and the lower IVC increases to a predetermined amount, about 40-50 mm Hg, the specially designed section of the stent wall temporarily collapses inward, allowing enough blood to leak around the valve to reduce the upper IVC pressure back below the predetermined pressure.

The predetermined pressure may be controlled by controlling the number, size, material, cross-section, and/or shape of the stent struts at the pressure relief feature. For example, the pressure required to open the pressure relief feature and allow retrograde blood flow through the device could be increased by including additional stent struts in the region neighboring the pressure relief feature. As another example, the stent struts in the area that comprises the emergency pressure relief feature may have a winding geometry, featuring some number of bend points, which act to increase the effective beam length of the struts. The increased effective beam length of the struts effectively reduces the amount of pressure required to collapse the stent wall and open the emergency pressure relief feature. The predetermined pressure may also be controlled by controlling the shape and size of the leaflet(s) attached to the emergency pressure relief feature. For example, the leaflets may be attached to the stent struts in a manner that billows slightly, thereby increasing the overall surface area of the leaflet, and reducing the pressure differential required to open the pressure relief feature. Additionally, the location and number of attachment points at the site of the emergency pressure relief feature may be used to control the size and shape of the pressure relief opening.

Although two leaflets are shown in FIG. 2, the pressure control feature of FIG. 2 may be made of any number of leaflets. There may also be multiple pressure relief features of the same type pictured in FIG. 2. For example, a four leaflet valve may be used as a pressure control feature, where two of the leaflets are also utilized as emergency pressure relief features by being designed to exert a radially inward directed force onto the stent wall as the pressure differential across the device increases. As another example, a three leaflet valve is contemplated, where one of the leaflets is designed to exert a radially inward force on a section of the stent wall such that the pressure control device allows for paravalvular leakage at a predetermined pressure differential.

Figure 3:
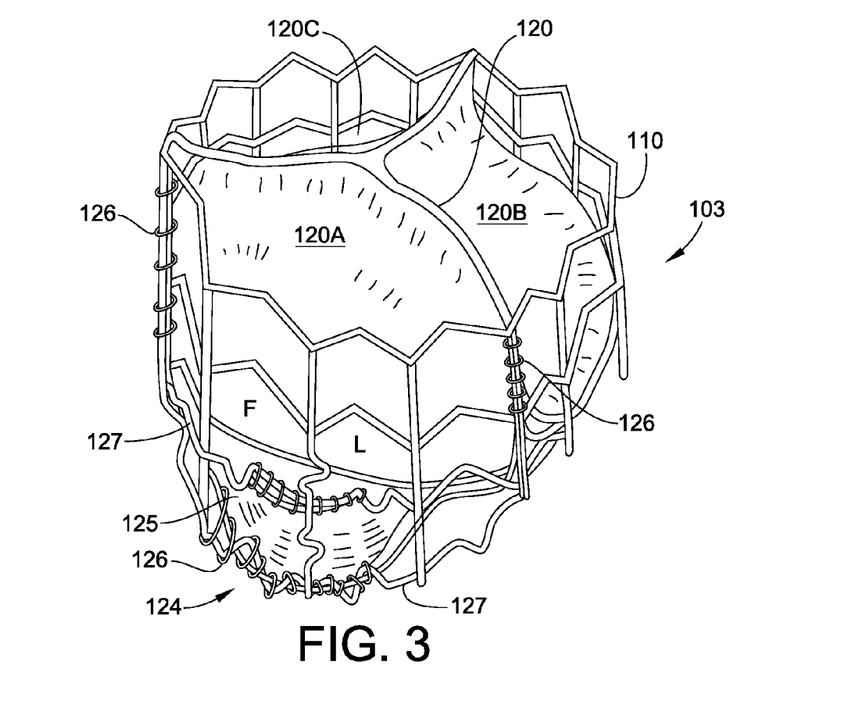
FIG. 3 depicts a third embodiment of a pressure-reducing device.

Turning now to FIG. 3, a pressure control device 103 is shown, consisting of a valve 120 and a tubular stent member 110. The valve 120 is shown with three leaflets (120 A-C), although any number of leaflets may be used. The pressure control device 103 includes an emergency pressure relief system 124, composed of a specially shaped leaflet 125 connected by various connecting sutures 126 to a section of the stent 110 which features bending or tortuous struts 127. These struts, which may also be of reduced cross section or thickness, act to reduce the stiffness of the stent around the region of the pressure relief system. The leaflet 125, or more than one if so provided, provides a large surface area supported by surrounding struts 127, especially struts with reduced stiffness or cross-sectional area. The force acting on the leaflet, e.g., higher blood pressure on one side of pressure control device 120 than the other, will be proportional to the area of the leaflet. The struts may then be directed so that if the pressure difference is more than a nominal value, say 50 mm Hg, the struts will strain and deflect, e.g., they will move and allow blood from the area of the renal veins to flow in the general direction of the heart and the right atrium.

The reduced stiffness of the stent around the pressure relief region allows deflection of the struts and flow of blood in a retrograde direction when the pressure about the pressure control device is higher than the pressure below the device. The reduced stiffness of the stent in one area provides a way for controlling the size and location of the pressure relief feature. By careful design, the pressure at which the pressure relief feature is activated is also selected. In addition, the pressure-accommodating struts may also be made only with reduced thickness or cross section, rather than the bending or twisting features depicted in FIG. 3.

In the embodiment of FIG. 3, the stent struts are designed so that under ordinary conditions, the struts exert a known or predetermined amount of pressure outward onto the wall of the IVC. For example, a tubular stent may be formed with a diameter which is generally larger than the internal diameter of a patient's IVC. This stent could then be collapsed down to a smaller delivery diameter, and delivered into the lumen, and then expanded or allowed to expand up to the internal diameter of the lumen. For example, the stent may be made of a shape-memory alloy, such as Nitinol, that will recover its trained shape when it is warmed from a cooler temperature to body temperature upon implantation within the patient when the alloy transforms from martensite to its trained austenite state. The stent would then continue to exert an outward force on the lumen as a result of the elastic properties of the stent structure. This predetermined pressure may be controlled in the same manner as detailed above for controlling the predetermined emergency relief pressure. The outward pressure allows the pressure relief feature to open only when the pressure in the IVC above the valve, i.e., the pressure felt in the right atrium of the heart, reaches a well defined threshold. In this way the pressure control feature only allows retrograde flow through the device when such flow would be beneficial to the patient. In one embodiment, the pressure differential across the valve is about 50 mm Hg when the valve reopens in response to the higher pressure. In other embodiments, a different relief pressure value may be used to open the valve.

Embodiments such as those of FIGS. 2 and 3 allow for true control of the venous pressures, by controlling both the pressure in the lower IVC and renal veins, but by also controlling the maximum allowable pressure in the upper IVC, hepatic veins, and right atrium (RA) of the heart. In one embodiment, the pressure relief feature is configured to allow blood to flow retrograde through the device when the pressure in the upper IVC exceeds the pressure in the lower IVC by about 50 mm of mercury. Other embodiments may be designed for higher or lower pressure differentials as desired and by using the techniques discussed, such as 30 mm or 20 mm.

Figure 4:
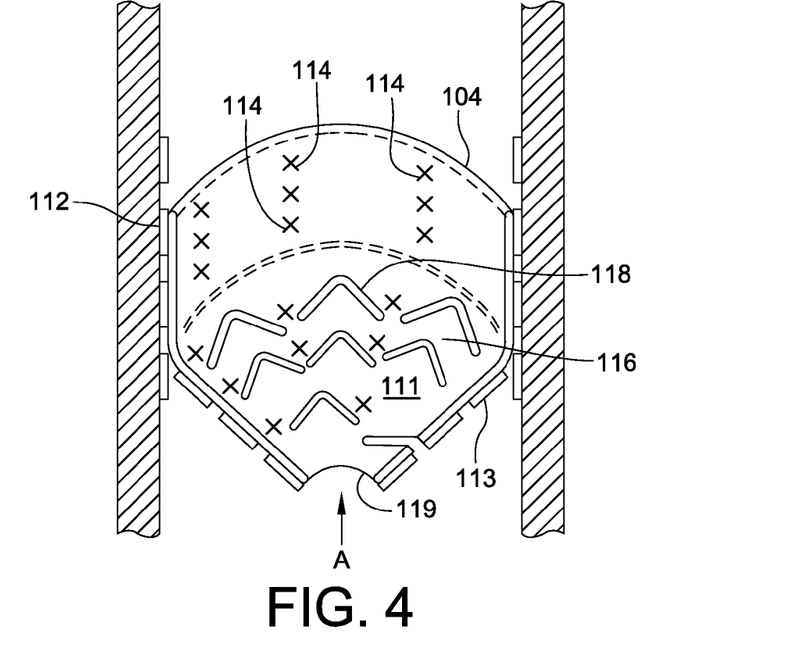
FIG. 4 depicts a fourth embodiment of a pressure-reducing device.

Turning now to FIG. 4, another embodiment of the present invention is shown. Depicted in FIG. 4 is a novel pressure control device 104 shown in a cross-sectional view. The pressure control device 104 features a stent-like outer body 112 with a truncated conical section 113, i.e., a frustoconical section. A sheet 111 of biocompatible material is connected to the conical section 113 of the pressure control device by an attachment or by connectors, such as sutures 114. The biocompatible sheet material features a plurality of slits 118 as shown, or cut outs which create tissue flaps 116. The sheet material 111 rests inside the frustoconical section 113, and is attached such that when blood is flowing normally from the lower IVC to the upper IVC the slits 118 expand or open, allowing blood to flow through with minimal impedance. One way to accomplish this is to arrange the biocompatible sheet on the inside of the stent, with the flaps slightly larger than the slits.

When the pressure in the upper IVC is greater than that of the pressure below the device, the slits 118 are configured such that they will close. For example, the tissue flaps 116 may be configured to reside on the inside of sheet 111 and may be slightly larger than the slits 118, such that the flaps 116 will rest against the conic section 113 of the pressure control device. In this way, the conic section 113 of the pressure control device prevents the tissue flaps 116 from relapsing. The base of the conic section 113 comprises an opening 119 that remains open at all times, allowing some predetermined amount of blood to flow past the device in either direction at any time. In one embodiment this opening may range from 3-5 mm. This feature may be used as a means to ensure that the upper IVC venous pressure does not spike to levels that may be considered unhealthy or unsafe.

The biocompatible sheet material may be any relatively flat material that is suited for implantation, including polymeric materials such as EPTFE or polyester, such as Dacron® polyester. In one embodiment of the present invention, the biocompatible sheet material is made from mammalian tissue, including mammalian pericardium. Such tissue can come from any number of sources, including ovine, bovine, porcine, or equine pericardium. In addition, the tissue may be chemically treated with any of the treatment chemicals disclosed above.

The slits 118 or tissue flaps 116 may be created by any number of means. For example, the slits may be cut into the biocompatible sheet by a die cutting or laser cutting. There may be any number of different slits, including two or three large elongate slits, or a multitude of smaller slits. The slits may be any number of shapes, including 'V' shaped cutouts as depicted in FIG. 4. Additional shapes include elongate horizontal cuts, elongate vertical cuts, square shaped cuts, or semicircular or elliptical cut outs. The cuts may be configured to produce a true flap or instead may be simple slits.

In one embodiment the attachments comprise sutures connecting the biocompatible sheet material to the conical section 113. In one embodiment, the truncated conical section or frusto-conical section 113 has a dual purpose. It acts as both a pressure controlling device, preventing high venous pressures from damaging key organs in the body. As the same time, due to the novel conical shape of the implant, the device simultaneously may act as an IVC filter, preventing large clots from becoming pulmonary emboli.

Figure 5:
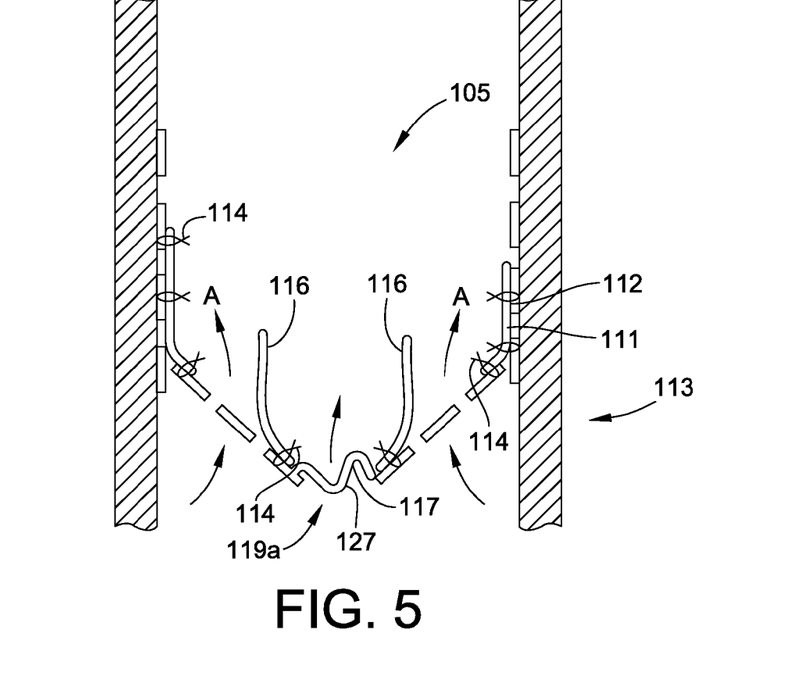
FIG. 5 depicts a fifth embodiment of a pressure-reducing device.
Figure 6:
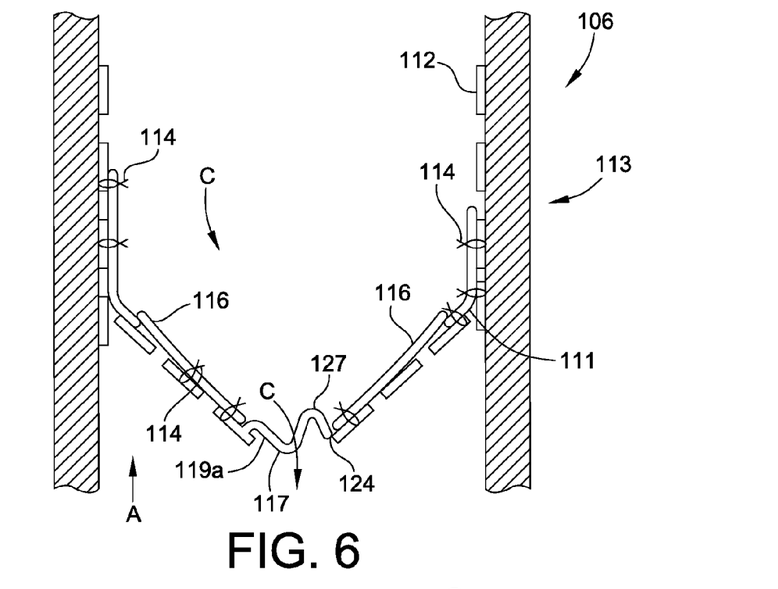
FIG. 6 depicts a sixth embodiment of a pressure-reducing device.

FIGS. 5 and 6 depict alternative embodiments, again including a stent-like outer body with a conical section. In FIGS. 5 and 6 at least one flat sheet of biocompatible material 111 is again attached at various attachment points to the conic section 113 of the pressure control device. In FIG. 6 the pressure control device 105 is shown when blood flow in the upper IVC is greater than the pressure in the lower IVC, and the flaps have closed, effectively blocking off a large amount of the cross-section of the vein, and increasing the resistance to normal blood flow through the device, while allowing a small retrograde flow through a pressure relief feature 119A, as shown by arrows C.

Still referring to the embodiments depicted in FIGS. 5 and 6, at the narrowest point of the conical section there exists a small opening 119A, which features a ring of elastic material 117. The elastic material may be made of any of the above cited materials that the stent body may be made of. In a preferred embodiment, the ring of elastic material 117 is made of a super-elastic nitinol alloy. The ring of elastic material is designed with convoluted struts 127, allowing the elastic material to stretch more easily. This allows the ring to stretch under a predetermined load, such as a predetermined back pressure from the upper IVC and ultimately from the pressure in the right atrium of the patient's heart. This feature may be used to help control the upper limit of the upper venous pressures that the device allows. As the pressure differential approaches what may be considered a dangerous level, the elastic ring expands, allowing additional blood to flow retrograde through the device and equalizing the pressure in the veins. By controlling the thickness of the struts, and the area of the attached bio-compatible material, one skilled in the art may control the pressure required to expand the ring a preset amount. In one embodiment, the elastic ring is configured to substantially increase in size when the difference in pressure in the upper IVC as compared to the lower IVC approaches 50 mm of mercury.

Figure 7:
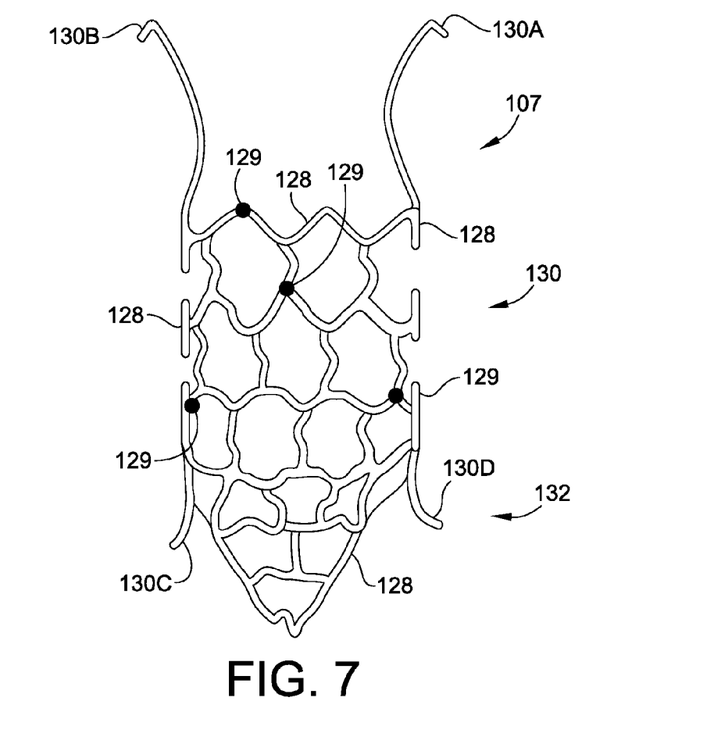
FIG. 7 depicts a stent useful in forming a pressure-reducing device.

FIG. 7 shows a stent member 107 with a conical section that may be used in conjunction with the already disclosed biocompatible sheet material with slits or flaps. The stent body is shown with various fixation members for fixing the device within the IVC. Stent 107 may be used, for example, with the other components discussed with respect to FIGS. 4-6. Stent 107 includes an upper cylindrical portion 130 and a lower frustoconical section 132. The stent is formed of a plurality of short stent portions or struts 128 joined at apices or junctions 129 to form a network or mesh. The materials for the struts, discussed above, may include Nitinol or other shape-memory alloys, and may also include stainless steels, such as 304, 304L, 316 and 316L, among others, and MP35 alloy.

Figure 8:
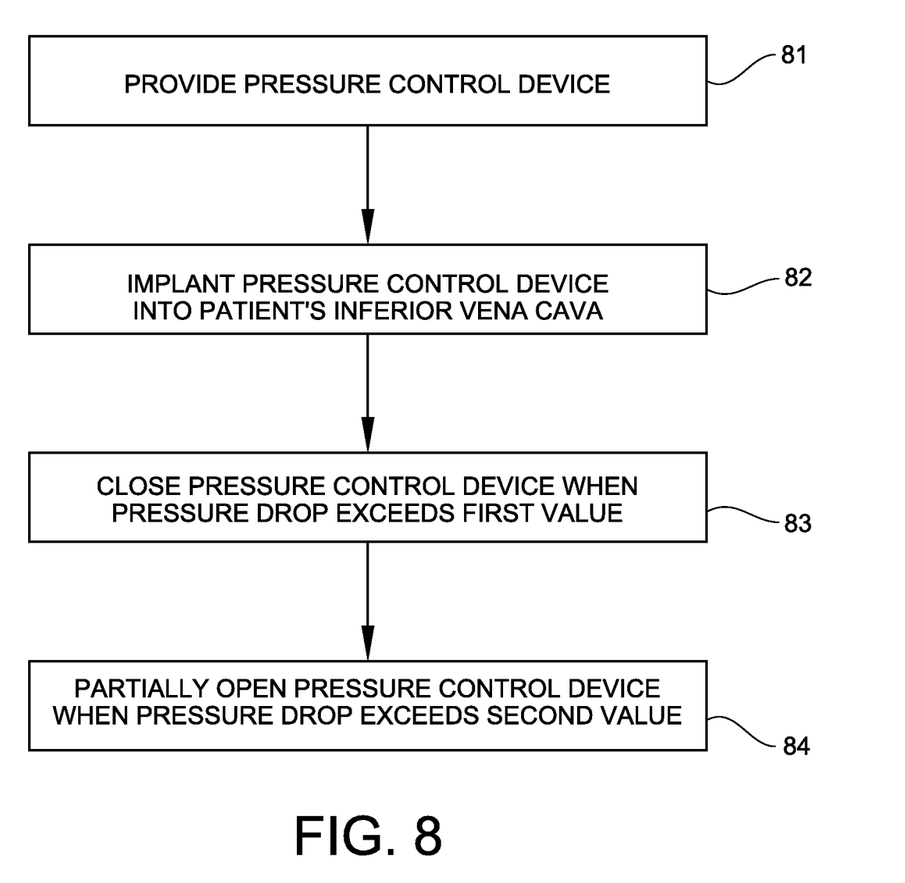
FIG. 8 depicts a method of deploying the pressure-reducing device.

The method described herein for reducing blood pressure in a patient's inferior vena cava, i.e., the patient's venous blood pressure, may be described in the flow chart depicted in FIG. 8. A first step 81 of the method is to provide a pressure control device, as described above. The device is then implanted 82 into the patient's inferior cava. The device acts as a normally-open valve, allowing blood to flow in the patient's inferior vena cava, from the renal veins toward the heart generally. One embodiment of the device is a flap valve, i.e., a valve with a plurality of one-way flaps. Pressure may build up across the device, indicating that there is higher blood pressure in the upper portions of the inferior vena cava and in or near the right atrium of the heart. One or more of the flaps may then close 83. With the valve closed or partially closed, the amount of venous blood flowing from the renal veins is reduced, thus reducing the pressure in the upper portion of the inferior vena cava and in the right atrium of the heart. It is possible that pressure may continue to build in the IVC and in the right atrium. It is obviously not good to stop blood flow within the body for a long period of time. Accordingly, if the pressure differential across the valve exceeds a second value, the valve then opens or partially opens 84 and allows blood to flow.

While reference has been made to various drawings and embodiments, it should be understood that certain substitutions, additions, and exchanges may be made by those skilled in the art while still remaining within the scope of the invention. The scope of the invention should therefore be defined by the attached claims:

What is claimed is:

1. A device for treating heart failure of a patient, comprising:
   a stent for implantation in an inferior vena cava of the patient;
   at least one pressure control feature configured to prevent elevated blood pressure from damaging an organ or vessel, wherein the at least one pressure control feature is configured to allow blood flow in a first direction and to resist flow in a second direction opposite to the first direction blood flow in the first direction is allowed when a pressure on a first side of the device exceeds a pressure on a second side of the device by a first value; and
   at least one connector joining the at least one pressure control feature to said stent,
   wherein the stent comprises a pressure relief feature comprising a reversibly collapsible portion of the stent configured to reversibly collapse to permit blood to flow in the second direction and reduce pressure differential across the device when the pressure on the second side of the device exceeds the pressure on the first side of the device by a second value, the second value greater than the first value, and wherein the stent, not including the reversibly collapsible portion, is configured to maintain substantial circumferential contact with the inferior vena cava when the reversibly collapsible portion collapses.

2. The device of claim 1, wherein the at least one pressure control feature comprises a plurality of flaps which are open to allow blood flow in the first direction and which are designed to begin to close when a pressure drop across the device is at least 10mm Hg.

3. The device of claim 1, wherein the at least one connector is selected from the group consisting of a suture and a crimping member.

4. A device for treating heart failure, comprising:
an elongate tubular member;
at least one pressure control feature;
and
a connector joining said at least one pressure control feature to said elongate tubular member,
wherein the at least one pressure control feature is configured for implantation in a blood vessel to prevent elevated blood pressure from damaging an organ or a vessel by allowing blood flow in a first direction and resisting blood flow in a second direction opposite to the first direction blood flow in the first direction is allowed when pressure on a first side of the device exceeds pressure on a second side of the device by a first value, and
wherein the elongate tubular member comprises a reversibly collapsible portion as a pressure relief feature configured to reversibly activate and reduce pressure differential across the device when the pressure on the second side of the device exceeds pressure on the first side of the device by a second value by allowing blood flow in the second direction, the second value greater than the first value, and wherein the elongate tubular member is configured to maintain substantial circumferential contact with the blood vessel into which said elongate tubular member is implanted when the reversibly collapsible portion collapses.

5. The device of claim 4, wherein the at least one pressure control feature comprises at least one flexible flap and wherein the reversibly collapsible portion comprises at least one flexible portion of a circumferential wall of the elongate tubular member.

6. The device of claim 4, wherein the at least one pressure control feature comprises a portion of a flexible flap attached to a circumferential wall of the elongate tubular member.

7. The device of claim 4, wherein the reversibly collapsible portion comprises at least one portion of a circumferential wall of the elongate tubular member having a reduced cross section or thickness.

8. A device to reduce venous pressure comprising:
a stent adapted to exert an outward radial force upon a lumen of an inferior vena cava, wherein the stent comprises an emergency pressure relief feature comprising a reversibly collapsible portion of the stent, and wherein the stent, not including the emergency pressure relief feature, is configured to maintain substantial circumferential contact with the inferior vena cava when the reversibly collapsible portion collapses;
at least one anchor integral with said stent adapted to contact a surface of said lumen; and
a valve having a first side and a second side and is configured to allow blood to flow in a first direction, wherein said first direction is a normal direction of blood flow and wherein said normal direction of blood flow is from said first side of the valve to said second side of the valve and wherein said valve is configured to close when a venous pressure on the second side of the valve exceeds a venous pressure on the first side of the valve by a first predetermined amount, and
wherein the emergency pressure release feature is configured to allow blood to flow retrograde in a direction opposite to the normal direction while said valve is at least partially closed and when the venous pressure on the second side of the valve exceeds a venous pressure on the first side of the valve by a second predetermined amount, the second predetermined amount greater than the first predetermined amount.

9. The device of claim 8, wherein the valve comprises a plurality of flexible flaps connected to the stent.

10. The device of claim 8, wherein the reversibly collapsible portion comprises a circumferential portion of the stent.

11. A device to reduce venous pressure comprising:
a stent adapted to exert an outward radial force upon a lumen of an inferior vena cava, wherein the stent comprises an emergency pressure relief feature comprising a reversibly collapsible portion of the stent, and wherein the stent, not including the emergency pressure relief feature, is configured to maintain substantial circumferential contact with the inferior vena cava when the reversibly collapsible portion collapses;
at least one anchor integral with said stent adapted to contact a surface of said lumen; and
a valve having a first side and a second side and is configured to allow blood to flow in a first direction, wherein said first direction is a normal direction of blood flow and wherein said normal direction of blood flow is from said first side of the valve to said second side of the valve and wherein said valve is configured to close when a venous pressure on the second side of the valve exceeds a venous pressure on the first side of the valve by a first value,
wherein the emergency pressure relief feature is configured to open to allow blood to flow retrograde in a direction opposite to the normal direction while said valve is at least partially closed and when the venous pressure on the second side of the valve exceeds a venous pressure on the first side of the valve by a second value, the second value greater than the first value.

\* \* \* \* \*